US010952440B2

(12) United States Patent
Quillet et al.

(10) Patent No.: US 10,952,440 B2
(45) Date of Patent: Mar. 23, 2021

(54) PARAFFINIC PHYTOSANITARY OIL COMPOSITION

(71) Applicant: TOTAL MARKETING SERVICES, Puteaux (FR)

(72) Inventors: Serge Quillet, Viroflay (FR); Eric Bureau, St-Hilarion (FR); Serge Cukierman, Neuilly sur Seine (FR); Louis Plancq, Levallois-Perret (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 16/093,945

(22) PCT Filed: Apr. 7, 2017

(86) PCT No.: PCT/FR2017/050837
§ 371 (c)(1),
(2) Date: Oct. 15, 2018

(87) PCT Pub. No.: WO2017/178738
PCT Pub. Date: Oct. 19, 2017

(65) Prior Publication Data
US 2019/0110479 A1    Apr. 18, 2019

(30) Foreign Application Priority Data
Apr. 15, 2016 (FR) ...................... 1653333

(51) Int. Cl.
| | | |
|---|---|---|
| *A01N 61/02* | (2006.01) |
| *A01N 27/00* | (2006.01) |
| *A01N 25/02* | (2006.01) |
| *A01N 25/04* | (2006.01) |
| *A61K 31/01* | (2006.01) |
| *A61K 35/06* | (2006.01) |
| *A61P 31/10* | (2006.01) |

(52) U.S. Cl.
CPC ............. *A01N 61/02* (2013.01); *A01N 25/02* (2013.01); *A01N 27/00* (2013.01); *A01N 25/04* (2013.01); *A61K 31/01* (2013.01); *A61K 35/06* (2013.01); *A61P 31/10* (2018.01)

(58) Field of Classification Search
None
See application file for complete search history.

(56) References Cited

U.S. PATENT DOCUMENTS

| | | |
|---|---|---|
| 2012/0010109 A1 | 1/2012 | Westelynck et al. |
| 2012/0245232 A1 | 9/2012 | Bousque et al. |
| 2014/0336279 A1 | 11/2014 | Bureau |
| 2016/0281009 A1 | 9/2016 | Aubry et al. |
| 2018/0125766 A1 | 5/2018 | Rodriguez et al. |

FOREIGN PATENT DOCUMENTS

| | | | |
|---|---|---|---|
| EP | 0 255 871 A2 | 2/1988 | |
| EP | 0255871 A2 * | 2/1988 | ........... C09D 11/033 |
| WO | 03/073858 A2 | 9/2003 | |
| WO | 2005/074687 A1 | 8/2005 | |
| WO | 2013/092977 A1 | 6/2013 | |
| WO | WO-2013092977 A1 * | 6/2013 | ............. A01N 25/04 |

OTHER PUBLICATIONS

Chemical Economics Handbook, Paraffins (C9-C17), Normal, Dec. 2019. (Year: 2019).*
Beattie et al., "Spray Oils Beyond 2000—Sustainable Pest and Disease Management," Proceedings of a conference held from Oct. 25 to 29, 1999 in Sydney, New South Wales, Australia, Jun. 2002, pp. 1-627.
Jul. 18, 2017 International Search Report issued in International Patent Application No. PCT/FR2017/050837.
Jul. 18, 2017 Written Opinion issued in International Patent Application No. PCT/FR2017/050837.

* cited by examiner

*Primary Examiner* — Melissa S Mercier
(74) *Attorney, Agent, or Firm* — Oliff PLC

(57) ABSTRACT

A phytosanitary composition including at least one paraffinic hydrocarbon fraction that includes isoparaffins, normal paraffins and naphthenes, wherein the content by weight of naphthenes ranges from 10 to 50% in relation to the total weight of the composition, and the weight ratio of the normal paraffins to the isoparaffins is greater than or equal to 0.30, in a carrier suitable for the phytosanitary treatment of plants.

18 Claims, No Drawings

PARAFFINIC PHYTOSANITARY OIL COMPOSITION

FIELD OF THE INVENTION

The invention relates to a composition based on phytosanitary oil of paraffinic hydrocarbon fraction type for the treatment of plant cryptogamic diseases and also to the treatment method and the use of this hydrocarbon fraction and of this composition in a preventive and curative manner, in particular on the first stages of plant cryptogamic diseases.

TECHNICAL CONTEXT OF THE INVENTION

A cryptogamic disease or fungal disease, is a disease caused in a plant by a fungus or another parasitic filamentous organism. Among these diseases, mention may in particular be made of black Sigatoka disease or else oidium. Fungal spores, usually transported by the wind, are deposited on plants, germinate and penetrate into the tissues of the plant. The fungus passes through the natural orifices (stomata, lenticels) or penetrates via injuries (in particular those caused by insects or by branch prunings), or else by passing through the plant cuticle.

Black Sigatoka disease or black leaf streak disease of the banana plant, caused by the ascomycete fungus *Mycosphaerella fijiensis*, and yellow Sigatoka disease, caused by ascomycete fungus *Mycosphaerella musicola*, are the most destructive leaf diseases in banana cultivation. The attacks reduce photosynthesis and, if the number of functional leaves is insufficient between flowering and harvesting, the bunch ripens prematurely while unpicked, thus depriving the producer of the sale thereof.

In the case of Sigatoka disease, the disease can be controlled by using various types of fungicides. Contact fungicides act when they are in contact with the fungus. Systemic fungicides have to be absorbed by the plant in order to act. The use of fungicides makes it possible to combat Sigatoka disease in commercial plantations, but their effects on the environment are worrying. Although it is possible to substantially reduce the number of treatments if the latter are carried out in the context of a reasoned control, *Mycosphaerella fijiensis* and *M. musicola* strains have developed resistance to numerous systemic products in all regions of production in the world (i.e. in Latin America, in the Caribbean, in Africa and in Asia).

It is known practice to use phytosanitary compositions to protect crops, these compositions being able to perform the role of a fungicide or else of an insecticide. They are generally sprayed onto the crops in the form of solutions in water or of water/oil or oil/water emulsions, in the presence of surfactant additives. The oil itself has a well-known fungistatic effect, contributing to slowing down the development of the disease.

For a long time, oils of petroleum origin, emulsified in water, have been sprayed onto crops for insecticide purposes. Suitably prepared, such oils make it possible to affect the fungi and parasites while at the same time having no negative effect on the development of the plants. Among conventional refined oils, obtained from crude petroleum and/or distillates resulting from refining, by solvent extraction or by hydroprocessing of base oils, the manufacturer would choose those that will be the least toxic but the most efficient, for example against insects and/or fungal attacks. It has thus been noted that, the more paraffinic the oil produced, that is to say the more the oil comprises compounds with a linear or branched, saturated carbon chain, the more efficient said oil will be against insects and the less phytotoxic it will be to plants.

However, even in very broad publications, such as *Spray Oils Beyond* 2000: *Proceedings of a conference held from* 1999 *in Sydney*, Published by the University of Western Sydney, Australia, dealing with the instance of the nature of the oil (purity, average number of carbons, fraction range, etc.), or else in the publications by the Centre de coopération Internationale en Recherche Agronomique pour le Développement (CIRAD) [French Agricultural Research and International Cooperation Center for Development], having worked on this subject since the 1950s, in particular on tropical crops, no information is found regarding a difference in performance associated with the intrinsic characteristics of paraffin oil. Only the importance of a high paraffin content, without any distinction made regarding these paraffins, is widely described.

The products encountered on the market for the treatment of Sigatoka disease generally have a kinematic viscosity at 40° C. ranging from 10 to 20 cSt and cold properties improved by means of a solvent deparaffining or catalytic deparaffining process. Furthermore and to date, a relationship between viscosity of phytosanitary paraffinic compositions and fungistatic efficacy was commonly made by those in the profession. Indeed, it is to date considered that a high viscosity allows the oil applied to remain on the leaves to be treated for a longer period of time and thus to be more effective. However, with a high viscosity, such as that of the majority of the oils generally used in the field, the oil composition used remains on the leaves of the treated plants for a sustained period of time and can thus affect the metabolism of the plants by reducing the photosynthetic capacity thereof.

Furthermore, in *Spray Oils Beyond* 2000: *Proceedings of a conference held from* 1999 *in Sydney*, Published by the University of Western Sydney, Australia, it is indicated that the carbon chains comprising more than 26 carbon atoms can result in chronic phytotoxicity.

Various processes for the fungicidal treatment of crops are described in the literature. Application WO 03/073858 describes a process for combating plant diseases by inhibition of the extracellular enzymes of the contaminating microorganisms. This application demonstrates the efficacy of boron, in boric acid form, in the inhibition of extracellular degrading enzymes. However, such aqueous solutions or suspensions are not suitable for aerial spreading in solution. Furthermore, this composition has proved to be phytotoxic with regard to certain plants at the effective concentrations. Finally, its efficacy with regard to certain diseases such as Sigatoka disease has not been proved. Also known, through document WO 2005/074687, is a process for the treatment of diseases of the banana plant by application of a polyene antibiotic, preferentially natamycin. This antibiotic is dissolved in water and sprayed onto the plants, or said plants are bathed therein. The repeated use of such an antibiotic has a risk of the appearance of resistances and is therefore a danger to ecosystems.

Document FR 2 953 369 describes an emulsifiable concentrate for a phytosanitary composition, comprising more than 90% by weight of at least one mixture of hydrocarbons of distillation fraction greater than 250° C., comprising less than 20% by weight of n-paraffins and less than 1% of aromatics, and from 1% to 4% by weight of a mixture of at least two surfactants TA1 and TA2, such that TA2 is more hydrophobic than TA1 and of which the HLB of the mixture ranges from 6 to 10. The weight content of the n-paraffin concentrate relative to the total amount of hydrocarbon fraction is therefore strictly less than 20%. In practice, isoparaffins represent therein more than 90% of the total paraffins. The phytosanitary activity illustrated is an insecticidal activity on citrus fruit crops.

Document FR 2 984 690 relates to the use of an oil emulsion as an acaricide or insecticide and for the antifungal treatment of the stems and leaves of a plant during the growth thereof in confined cultivation spaces, at high cultivation intensity. The emulsion comprises water and a petroleum-derived paraffin oil which has a boiling point of from 200° C. to 450° C., a viscosity of less than or equal to 20 mm$^2$/s at 40° C., and an unsulfonatable residue content of at least 95% according to the standard ASTM D483. The compositions are tested for their acaricidal activity and their activity against oidium on rosebush crops. The compositions described in this document comprise a very low n-paraffin content relative to the isoparaffin content.

FR 2 999 190 discloses a process for obtaining a hydrocarbon fraction, comprising deparaffining and hydrodearomatization steps. The objective of this prior art document is to obtain fractions with a low sulfur and aromatic content.

EP 0 255 871 describes a hydrocarbon fraction and the use thereof as an ink solvent. Said hydrocarbon fraction must be non-toxic, with an improved odor and must have a high solvent capacity for resins.

None of these documents describes the use of a hydrocarbon fraction with an n-paraffin content which is controlled relative to the isoparaffin content, for the phytosanitary treatment of plants.

There therefore remains the need to have available a composition for treating cryptogamic diseases of plants, which is effective and non-toxic to the user, the plant or the environment. The profession is constantly searching for solutions that can improve the performance level of the existing compositions.

The applicant has found, surprisingly, that this need can be met by means of a novel phytosanitary oil composition for the treatment of crops.

An objective of the present invention is to provide optimization of the performance level of the current treatments for cryptogamic diseases of cultivated plants.

The objective of the present invention is to provide a composition with increased effectiveness for the treatment of cryptogamic diseases of plants. The objective of the invention is in particular to provide a composition that can be used as an adjuvant for an active ingredient in the treatment of cryptogamic diseases of plants.

In particular, the composition of the invention is particularly suitable for improving the performance levels of compositions for treating plants of tropical and equatorial regions.

In particular, the composition of the invention is particularly suitable for improving the performance levels of compositions for treating crops with a view to reducing, limiting, preventing, avoiding the development of black Sigatoka disease or black leaf streak disease of the banana plant, caused by the ascomycete fungus *Mycosphaerella fijiensis* and/or of yellow Sigatoka disease caused by the ascomycete fungus *Mycosphaerella musicola*.

The compositions of the invention have the advantage of not blocking photosynthesis and of not slowing down plant growth.

The objective of the present invention is also to provide a composition for treating cryptogamic diseases which has a suitable viscosity, that is to say without the risk of impairment of the metabolism of the plant.

SUMMARY OF THE INVENTION

These objectives are achieved by virtue of a novel phytosanitary composition.

The invention relates firstly to a phytosanitary composition comprising at least one paraffinic hydrocarbon fraction which comprises isoparaffins, normal paraffins and naphthenes, the weight content of naphthenes ranging from 10% to 50% relative to the total weight of the composition, the weight ratio of the normal paraffins relative to the weight of the isoparaffins being greater than or equal to 0.30, in a carrier suitable for the phytosanitary treatment of plants.

The invention also relates to the use of a paraffinic hydrocarbon fraction which comprises isoparaffins, normal paraffins and naphthenes, the weight content of naphthenes ranging from 10% to 50% relative to the total weight of the composition, the weight ratio of the normal paraffins relative to the weight of the isoparaffins being greater than or equal to 0.30, for the phytosanitary treatment of plants.

The invention also relates to a process for the phytosanitary treatment of crops, comprising at least one step of application, preferably by sprinkling, spraying or spreading, of the phytosanitary composition according to the invention.

The invention also relates to an emulsifiable concentrated composition that can be used for the preparation of a phytosanitary composition according to the invention, comprising
    at least one paraffinic hydrocarbon fraction which comprises isoparaffins, normal paraffins and naphthenes, the weight content of naphthenes ranging from 10% to 50% relative to the total weight of the composition, the weight ratio of the normal paraffins relative to the weight of the isoparaffins being greater than or equal to 0.30,
    and
    at least one emulsifying agent.

According to one advantageous embodiment, the hydrocarbon fraction comprises a weight content of normal paraffins of greater than or equal to 15% and preferentially greater than or equal to 20%, relative to the total weight of the hydrocarbon fraction.

According to one advantageous embodiment, the hydrocarbon fraction comprises a weight content of isoparaffins of less than 75%, preferably less than or equal to 65% and preferentially less than or equal to 50%, relative to the total weight of the hydrocarbon fraction.

According to one advantageous embodiment, the hydrocarbon fraction comprises a weight content of naphthene compounds ranging from 15% to 45%, even more preferentially from 20% to 40%, relative to the total weight of the hydrocarbon fraction.

According to one advantageous embodiment, the hydrocarbon fraction is chosen from normal paraffins comprising from 15 to 30 carbon atoms, preferably from 16 to 27 carbon atoms and preferentially from 17 to 25 carbon atoms.

According to one advantageous embodiment, the hydrocarbon fraction comprises a weight content of unsulfonatable residues of greater than or equal to 92%, preferably greater than or equal to 95%, preferentially greater than or equal to 99%, relative to the total weight of the hydrocarbon fraction.

According to one advantageous embodiment, the hydrocarbon fraction has a boiling point ranging from 250 to 400°

C., preferably from 260 to 390° C., and preferentially from 270 to 380° C. according to the standard ASTM D86.

According to one advantageous embodiment, the hydrocarbon fraction has a kinematic viscosity at 40° C. ranging from 4 to 25 mm$^2$/s, preferentially from 5 to 20 mm$^2$/s and more preferentially from 5 to 10 mm$^2$/s according to the standard ASTM D445.

According to one advantageous embodiment, the hydrocarbon fraction has a pour point of greater than or equal to −5° C., preferably greater than or equal to 0° C. and preferentially greater than or equal to 5° C. according to the standard ASTM D97.

According to one advantageous embodiment, the hydrocarbon fraction represents an amount ranging from 1% to 99% by weight relative to the total weight of the composition.

According to one advantageous embodiment, the phytosanitary composition is in the form of an oil-in-water emulsion or of a water-in-oil emulsion.

According to one advantageous embodiment, the use is for an application by sprinkling on the crops, in particular by spraying or spreading.

According to one advantageous embodiment, the hydrocarbon fraction is formulated in the form of an oil-in-water emulsion or of a water-in-oil emulsion.

According to one advantageous embodiment, the use is intended for the preventive and/or curative treatment of cryptogamic diseases of plants.

According to one advantageous embodiment, the use is intended for the preventive and/or curative treatment of cryptogamic diseases of plants of tropical and equatorial regions.

According to one advantageous embodiment, the use is intended for the preventive and/or curative treatment of cryptogamic diseases of the banana plant.

According to one advantageous embodiment, the use is intended to reduce, limit, prevent, avoid the development of black Sigatoka disease or black leaf streak disease of the banana plant, caused by the ascomycete fungus *Mycosphaerella fijiensis* and/or of yellow Sigatoka disease caused by the ascomycete fungus *Mycosphaerella musicola*.

According to one advantageous embodiment, the process of the invention also comprises the joint application of at least one fungicidal active ingredient.

DETAILED DESCRIPTION OF THE INVENTION

The invention relates to the use of a phytosanitary oil composition comprising at least one hydrocarbon fraction derived from crude petroleum or one hydrocarbon fraction resulting from the conversion of biomass, for the treatment of cryptogamic diseases.

It relates to a phytosanitary composition comprising this oily composition in a carrier acceptable for a phytosanitary application.

As a preliminary, it will be noted that, in the description and the claims which follow, the expression "between" should be understood as including the limits cited.

Phytosanitary Oil Composition:

The phytosanitary oil composition according to the invention comprises at least one hydrocarbon fraction of petroleum origin or resulting from biomass.

The phytosanitary oil composition according to the invention preferably comprises a hydrocarbon fraction content ranging from 50% to 100%, preferably from 70% to 100%, more preferentially from 80% to 100% and ideally from 90% to 100% by weight, relative to the total weight of the phytosanitary oil composition.

The other components of the phytosanitary protective oil may be: oil-soluble phytosanitary active ingredients, oils of plant or animal origin, surfactants.

The suitable oils of biological origin are, for example, rapeseed oil, canola oil, tall oil, sunflower oil, soybean oil, hemp oil, olive oil, linseed oil, mustard oil, palm oil, peanut oil, castor oil, coconut oil, animal fats such as tallow, recycled food fats.

In particular, the phytosanitary oil composition may be in the form of an emulsifiable concentrate: surfactants are introduced into the oily composition so as to allow the production of an emulsion by simple mixing of this oily composition with an aqueous phase. The emulsifiable concentrate can comprise small amounts of water, oil-soluble phytosanitary active ingredients, oils of plant or animal origin.

Hydrocarbon Fraction:

The hydrocarbon fraction used in the composition according to the invention can also be referred to as hydrocarbon-based solvent. Advantageously, it essentially consists of paraffinic components and of naphthenes.

The hydrocarbon fraction used in the composition according to the invention preferably has a weight content of paraffinic compounds ranging from 50% to 100%, advantageously from 50% to 90%, preferably from 55% to 85% and more preferentially from 60% to 80%. These paraffins are generally mixtures of normal paraffins and of isoparaffins.

The hydrocarbon fraction used in the composition according to the invention comprises a significant content of normal paraffins. The term "significant content" is intended to mean that the weight content of normal paraffins of the hydrocarbon fraction is greater than 10%, preferentially the content of normal paraffins of the hydrocarbon fraction is greater than or equal to 15% by weight and more preferentially the content of normal paraffins of the hydrocarbon fraction is greater than or equal to 20% by weight, relative to the total weight of the hydrocarbon fraction.

The hydrocarbon fraction used in the composition according to the invention also comprises a weight content of isoparaffins of less than 80%, advantageously less than or equal to 75%, preferably less than or equal to 65%, preferentially less than or equal to 50%, relative to the total weight of the hydrocarbon fraction.

The hydrocarbon fraction used in the composition according to the invention also has a weight content of naphthene compounds ranging from 0 to 50%, advantageously from 10% to 50%, preferably from 15% to 45%, even more preferentially from 20% to 40%.

According to one preferred embodiment, the hydrocarbon fraction comprises a weight content of isoparaffins of less than or equal to 70%, of normal paraffins of greater than or equal to 15% and of naphthenes ranging from 10% to 50%. Preferentially, the hydrocarbon fraction comprises a weight content of isoparaffins of less than or equal to 65%, of normal paraffins of greater than or equal to 15% and of naphthenes ranging from 15% to 45%. More preferentially, the hydrocarbon fraction comprises a weight content of isoparaffins of less than or equal to 60%, of normal paraffins of greater than or equal to 20% and of naphthenes ranging from 20% to 40%.

Advantageously, the isoparaffins, the normal paraffins and the naphthenes represent at least 90% by weight relative to the total weight of the hydrocarbon fraction, preferably at least 95% by weight, even better still at least 98% and even more preferentially at least 99%.

The ratio of the weight of the normal paraffins relative to the weight of the isoparaffins in the hydrocarbon fraction is greater than or equal to 0.30, preferably greater than or equal to 0.35, even better still greater than or equal to 0.4. The applicant has discovered that a normal paraffin/isoparaffin weight ratio greater than the ratios disclosed in the prior art provides excellent results in the treatment of cryptogamic diseases.

The hydrocarbon fraction used in the composition according to the invention is advantageously at a very low aromatics content. The term "very low aromatics content" is preferably intended to mean a hydrocarbon fraction comprising a content of aromatic compounds of less than or equal to 1000 ppm, preferentially less than or equal to 500 ppm, even more preferentially less than or equal to 300 ppm, measured by UV spectrometry.

The hydrocarbon fraction also preferably has a sulfur content of less than or equal to 10 ppm, preferentially less than or equal to 5 ppm and more preferentially less than or equal to 2 ppm.

The hydrocarbon fraction used in the composition according to the invention preferably has a kinematic viscosity at 40° C. ranging from 4 to 25 mm$^2$/s, preferentially from 4 to 20 mm$^2$/s and more preferentially from 5 to 10 mm$^2$/s according to the standard ASTM D445.

The hydrocarbon fraction according to the invention preferably has a pour point according to the standard ASTM D97 of greater than or equal to −5° C., preferentially greater than or equal to 0° C. and more preferentially greater than or equal to 5° C.

The hydrocarbon fraction according to the invention also comprises a weight content of unsulfonatable residues according to the standard ASTM D483 of greater than or equal to 92%, preferably greater than or equal to 95% and more preferentially greater than or equal to 99%.

Such compositions of hydrocarbon fractions can be obtained in the following way. The hydrocarbon fraction according to the invention is a hydrocarbon fraction which can be derived in a known manner from crude petroleum or from biomass.

Preferably, for the purposes of the invention, the term "hydrocarbon fraction" is intended to mean a fraction resulting from the distillation of crude petroleum, preferably resulting from the atmospheric distillation and/or the vacuum distillation of crude petroleum, preferably resulting from atmospheric distillation followed by vacuum distillation.

The hydrocarbon fraction used in the composition of the invention is advantageously obtained by means of a process comprising hydrotreatment, hydrocracking or catalytic cracking steps.

The hydrocarbon fraction used in the composition of the invention is preferably obtained by means of a process comprising dearomatization and optionally desulfurization steps.

The hydrocarbon fraction according to the invention is not subjected to a dewaxing step. Dewaxing is a known process for treating hydrocarbon fractions without conversion, consisting in removing the paraffins and the microcrystalline waxes from a feedstock or in converting them into compounds of lower molecule weight and/or of different molecular structure. The dewaxing processes conventionally known are solvent-extraction or hydrodewaxing processes. During these processes, the normal paraffins are extracted or converted into isoparaffins in order generally to obtain a lower pour point. The term "dewaxing" is intended to mean a treatment process which makes it possible to obtain a hydrocarbon fraction comprising a weight content of normal paraffins of less than 10%. Processes resulting in partial dewaxing of the hydrocarbon fraction are not excluded from the invention.

Preferably, the hydrocarbon fraction obtained after the distillation step(s) is chosen from gas oil fractions or mineral oil fractions. The gas oil fraction is preferably obtained by means of a process comprising hydrotreatment, hydrocracking or catalytic cracking steps, optionally followed by dearomatization and optionally desulfurization steps. The mineral fraction is preferably obtained by means of a process comprising vacuum-distillation, solvent-extraction and optionally partial dewaxing and hydrotreatment or hydrocracking steps.

The hydrocarbon fraction may be a mixture of hydrocarbon fractions which have undergone the steps described above.

The hydrocarbon fraction used in the composition of the invention may also result from the conversion of biomass.

The expression "result from the conversion of biomass" is intended to mean a hydrocarbon fraction produced from raw materials of biological origin, preferably chosen from vegetable oils, animal fats, fish oils and mixtures thereof. Appropriate raw materials of biological origin are for example rapeseed oil, canola oil, tall oil, sunflower oil, soybean oil, hemp oil, olive oil, linseed oil, mustard oil, palm oil, peanut oil, castor oil, coconut oil, animal fats such as tallow or recycled food fats, raw materials resulting from genetic engineering, and biological raw materials produced from microorganisms such as algae and bacteria.

Preferably, the hydrocarbon fraction of biological origin is obtained by means of a process comprising hydrodeoxygenation (HDO) and isomerization steps. The hydrodeoxygenation (HDO) step results in the decomposition of the structures of the biological esters or of the triglyceride constituents, in the elimination of the oxygen-bearing, phosphorus-bearing and sulfur-bearing compounds and in the hydrogenation of olefinic bonds. The product resulting from the hydrodeoxygenation reaction is then isomerized. A fractionation step can preferably follow the hydrodeoxygenation and isomerization steps.

The fractions of interest are then subjected to hydrotreatment then distillation steps in order to obtain the specifications of the desired hydrocarbon fraction according to the invention.

The hydrocarbon fraction may be a mixture of hydrocarbon fraction resulting from the distillation of crude petroleum and/or from the conversion of biomass.

Preferably, the hydrocarbon fraction is a hydrocarbon fraction resulting from the distillation of crude petroleum.

Advantageously, the hydrocarbon fraction is a hydrogenated hydrocarbon fraction.

The hydrocarbon fraction used in the composition of the invention is advantageously a hydrocarbon fraction which has a distillation range DR (in ° C.) ranging from 250 to 400° C., preferably from 260 to 390° C. and even more preferentially from 270 to 380° C., measured according to the standard ASTM D86. Preferably, the difference between the initial boiling point and the final boiling point is less than or equal to 100° C. The hydrocarbon fraction may comprise one or more fractions having distillation ranges included in the ranges described above.

Advantageously, the hydrocarbon fraction used in the phytosanitary composition according to the invention is totally saturated. Preferably, the components of the hydrocarbon fraction are chosen from hydrocarbon-based chains comprising from 15 to 30 carbon atoms, preferentially from 16 to 27 carbon atoms, more preferentially from 17 to 25 carbon atoms.

According to a first embodiment, the hydrocarbon fraction preferably has:
- a boiling point ranging from 250 to 400° C., preferably from 260 to 390° C. and even more preferentially from 270 to 380° C., measured according to the standard ASTM D86,
- a kinematic viscosity ranging from 4 to 25 mm²/s, preferentially from 5 to 20 mm²/s and more preferentially from 5 to 10 mm²/s according to the standard ASTM D445, and According to a second embodiment, the hydrocarbon fraction preferably has:
- a kinematic viscosity ranging from 4 to 25 mm²/s, preferentially from 5 to 20 mm²/s and more preferentially from 5 to 10 mm²/s according to the standard ASTM D445, and
- a pour point according to the standard ASTM D97 of greater than or equal to −5° C., preferentially greater than or equal to 0° C. and more preferentially greater than or equal to 5° C.

According to one preferential embodiment, the hydrocarbon fraction has:
- a boiling point of from 250 to 400° C., preferably from 260 to 390° C. and even more preferentially from 270 to 380° C., measured according to the standard ASTM D86,
- a kinematic viscosity ranging from 4 to 25 mm²/s, preferentially from 5 to 20 mm²/s and more preferentially from 5 to 10 mm²/s according to the standard ASTM D445, and
- a pour point according to the standard ASTM D97 of greater than or equal to −5° C., preferentially greater than or equal to 0° C. and more preferentially greater than or equal to 5° C.

Phytosanitary Composition

The invention relates to a composition comprising the oily composition in a carrier suitable for a phytosanitary application with a view to the treatment of plants.

The expression "carrier suitable for the phytosanitary treatment of plants" is intended to mean a carrier which acts as a vehicle for the treatment of plants, in particular by sprinkling, spreading or any other means for treating plants. This carrier must be non-toxic to the plant and to its environment, in particular to human beings.

The carrier suitable for a phytosanitary application can consist of an oil-in-water emulsion, a water-in-oil emulsion, a dispersion or a suspension of oily particles in an aqueous phase.

In addition to an aqueous phase, the phytosanitary composition may comprise surfactants which make it possible to form an emulsion of the oily phase in the aqueous phase, such as for example nonionic surfactants, such as polyalkoxylated fatty acids, fatty acid esters of sorbitan, (poly)alkoxylated fatty acid esters of sorbitan, alkoxylated alkylphenols, alkoxylated fatty alcohols, fatty acid esters of glycerol, etc. It may comprise polymers which allow the stabilization of the emulsion or the dispersion or of the suspension.

The aqueous phase may comprise salts, and water-soluble phytosanitary active ingredients.

Additives:

The phytosanitary oil composition according to the invention may also be mixed with any other phytosanitary products (insecticides and/or fungicides) and also with adjuvants (emulsifiers, wetting agents, stabilizers, etc.) normally used in the phytosanitary field. Of course, those skilled in the art will take care to choose the optional other adjuvant(s) or additive(s) of the composition according to the invention in a manner such that the advantageous properties intrinsically associated with the phytosanitary composition in accordance with the invention are not or are not substantially impaired by the envisioned addition.

Without being limited to these and by way of example, mention may be made, as fungicides that can be used with the phytosanitary composition according to the invention, of contact products belonging to the dithiocarbamate family, such as Mancozeb, systemic products of the strobilurin family (azoxystrobin, pyraclostrobin, trifloxystrobin), those of the carboximide family (fluoryram, izopyrazam), the amine family (fenpropimorph, tridemorph, spiroxamine), the anilinopyrimidine family (pyrimethanil), dehydrogenase succinate inhibitors (boscalid) and sterol demethylation inhibitors (difenoconazole, epoxyconazole, fenbuconazole, propiconazole, tebuconazole).

Depending on the hydrophilic or lipophilic nature of these additives, they will be introduced into the aqueous phase or into the oily phase.

Advantageously, the treatment composition comprises a content of phytosanitary oil composition according to the invention ranging from 1% to 99% by weight relative to the total weight of the composition, advantageously from 10% to 80%, and more preferentially from 15% to 70%. The remainder of the composition consists, in a nonlimiting manner, of the aqueous phase, of optional additives, of surfactants, of polymers, of phytosanitary active ingredients, in particular fungicides. The latter, when they are used in the compositions of the invention, are so used at the doses usually recommended according to the type of plant and the seriousness of the disease.

Emulsifiable Concentrate

Preferably, the emulsifiable concentrate comprises a content of phytosanitary oil composition according to the invention ranging from 50% to 99% by weight, advantageously from 70% to 95% by weight, relative to the total weight of the concentrate.

Among the other components of the emulsifiable concentrate, mention may be made, in a nonexhaustive manner, of: emulsifying surfactants, stabilizers, salts, phytosanitary active ingredients and optionally water.

The emulsifying surfactants are chosen so as to allow the formation of a water-in-oil emulsion or an oil-in-water emulsion, a dispersion or a suspension of oily particles in an aqueous phase.

Preferably, the emulsifiable concentrate comprises at least one surfactant which makes it possible to form an emulsion of the oily phase in the aqueous phase, such as for example nonionic surfactants, such as polyalkoxylated fatty acids, fatty acid esters of sorbitan, (poly)alkoxylated fatty acid esters of sorbitan, alkoxylated alkylphenols, alkoxylated fatty alcohols, fatty acid esters of glycerol, etc.

Among the stabilizers, mention may be made of polymers which allow the stabilization of the emulsion or of the dispersion or of the suspension.

When it is present, the aqueous phase of the concentrate may comprise salts, and water-soluble phytosanitary active ingredients as have been described above.

Use of the Composition:

Another subject of the invention is the use of the phytosanitary oil composition as defined above, for the curative and/or preventive treatment of cryptogamic diseases of plants. It also relates to the use of the phytosanitary composition described above, preferentially a water-in-oil or oil-in-water emulsion, for the curative and/or preventive treatment of cryptogamic diseases of plants.

The invention relates more particularly to the preventive and/or curative treatment of cryptogamic diseases of plants of tropical and equatorial regions.

The invention relates more particularly to the preventive and/or curative treatment of cryptogamic diseases of the banana plant.

In particular, the composition of the invention is particularly suitable for the treatment of crops with a view to reducing, limiting, preventing, avoiding the development of black Sigatoka disease or black leaf streak disease of the banana plant, caused by the ascomycete fungus *Mycosphaerella fijiensis*, and/or of yellow Sigatoka disease caused by the ascomycete fungus *Mycosphaerella musicola*.

According to a first variant, the oily composition, or the phytosanitary composition, is used alone in the context of this application.

According to another variant of the invention, which variant is preferred, the oily composition, or the phytosanitary composition, is used in conjunction with a fungicidal treatment using at least one fungicidal active ingredient. In this case, the oily composition, or the phytosanitary composition, has the function of acting as an adjuvant to the fungicidal active ingredient and of reinforcing the action thereof against cryptogamic diseases.

Depending on the method of administration of the composition of the invention, in particular in conjunction with, or in the absence of, a joint treatment using a fungicidal active ingredient, the amounts and the frequencies of administration are adjusted by those skilled in the art.

Phytosanitary Treatment Method:

Finally, the invention also covers a phytosanitary treatment method comprising at least one step of sprinkling the plant to be treated, preferably by spreading or by spraying of the phytosanitary oil composition according to the invention on the plants to be treated. The treatment is advantageously applied on the aerial parts of the plants.

The treatment rate is advantageously from 0.5 to 20 liters of phytosanitary oil per hectare, preferably from 1 to 15 liters of phytosanitary oil per hectare. Depending on the dilution of the composition, the amount of phytosanitary composition sprayed, sprinkled or spread is adjusted.

The treatment is advantageously repeated at intervals of from 6 to 9 days, throughout the vegetative cycle.

According to a first variant of this method, the oily composition, or the phytosanitary composition, is administered alone in the context of this treatment.

According to another variant of the invention, which variant is preferred, the oily composition, or the phytosanitary composition, is administered in conjunction with a fungicidal treatment using at least one fungicidal active ingredient.

The term "in conjunction" is intended to mean the active ingredient can be diluted in the composition of the invention, but also that it can be administered in another composition, which is applied simultaneously or in alternating fashion with the composition of the invention.

Examples

In the remainder of the present description, examples are given by way of illustration of the present invention and are no way intended to limit the scope thereof.

Various phytosanitary compositions, according to the invention, and conventionally found in the field of the invention, were evaluated. This evaluation relates both to the fungistatic efficacy and the physicochemical properties of these phytosanitary compositions.

In the series of tests described below, the effect of the amount of normal paraffins contained in the oil was specifically evaluated.

Various hydrocarbon-based oils were thus evaluated.

The hydrocarbon-based oil A is a hydrocarbon-based oil according to the invention.

The hydrocarbon-based oil B is a comparative hydrocarbon-based oil. It is a paraffinic mineral oil resulting from the refining of petroleum and obtained by atmospheric distillation, vacuum distillation, hydrocracking and hydrotreatment.

The hydrocarbon-based oil C is a comparative mineral oil used for the formulation of phytosanitary products commonly found on the market under the tradename Banole HV. This hydrocarbon-based oil is a mineral oil widely used in the treatment of Sigatoka disease. It results from the refining of petroleum and is obtained by means of a process comprising, inter alia, a dewaxing step making it possible to obtain low pour points.

The hydrocarbon-based oil D is a comparative mineral oil used for the formulation of phytosanitary products commonly found on the market under the trade name Spraytex M100. This hydrocarbon-based oil results from the refining of petroleum and is obtained by means of a process comprising, inter alia, a dewaxing step making it possible to obtain low pour points.

The comparative oils C and D are conventionally found on the phytosanitary composition market.

Table 1 groups together the physicochemical properties of the various hydrocarbon-based oils formulated in the phytosanitary compositions evaluated.

The % are given by weight relative to the total weight of the components.

TABLE 1

| | | Hydrocarbon-based oils | | | |
|---|---|---|---|---|---|
| Characteristics | Standards | A (according to the invention) DEV1781 | B (comparative example) G400H Banole Oudale | C (comparative example) Calumet, Banole HV | D (comparative example) Spraytex M100SL |
| Sulfur (%) | ASTM D2622 | <0.001 | <0.001 | <0.001 | <0.001 |
| total paraffins (%) | GC2D | 69 | 75 | 65 | 65 |
| isoparaffins (%) | GC2D | 46 | 59 | 61 | 64 |
| n-paraffins (%) | GC2D | 23 | 16 | 1 | 1 |
| naphthene compounds (%) | GC2D | 31 | 25 | 35 | 35 |

TABLE 1-continued

|  |  | Hydrocarbon-based oils | | | |
|---|---|---|---|---|---|
| Characteristics | Standards | A (according to the invention) DEV1781 | B (comparative example) G400H Banole Oudale | C (comparative example) Calumet, Banole HV | D (comparative example) Spraytex M100SL |
| Normal paraffin/isoparaffin ratio | — | 0.50 | 0.27 | 0.016 | 0.015 |
| Hydrocarbon-based chain length | — | C18-C24 | C18-C22 | C20-C27 | C21-C30 |
| Initial boiling point (° C.) | ASTM D86 | 300 | 300 | 330 | 345 |
| Final boiling point (° C.) |  | 370 | 350 | 395 | 415 |
| Density at 15° C. (kg/m$^3$) | EN ISO 12185 | 822 | 817 | 857 | 852 |
| Flash point (° C.) | ASTM D93 | 160 | 158 | 186 | 200 |
| Aniline point (° C.) | ASTM D611 | 103 | 101 | 98 | 98 |
| Pour point (° C.) | ASTM D97 | 9 | 0 | −27 | −15 |
| Kinematic viscosity at 40° C. (cSt) | ASTM D445 | 8 | 6 | 15 | 19 |
| Unsulfonatable residues (%) | ASTM D483 | >99 | >99 | 95 | >99 |

Phytosanitary Compositions:

Various phytosanitary compositions were formulated in order for their fungistatic efficacy to be evaluated.

The various phytosanitary compositions exemplified comprise the hydrocarbon-based oils A to D according to table 1. Composition 1 is a phytosanitary composition according to the invention. Compositions 2 and 3 are comparative phytosanitary compositions. They comprise the same proportions of hydrocarbon-based oil as composition 1 according to the invention. Composition 4 is a reference comparative composition comprising the hydrocarbon-based oil D. This composition is found on the market of phytosanitary products intended for the treatment of Sigatoka disease of the banana plant and sold under the name Spraytex M 100 by the company Chevron. Composition 5 is a phytosanitary composition according to the invention which differs from composition 1 in that it comprises 20% less of hydrocarbon-based oil A compared with composition 1, the difference being made up of water.

Table 2 below indicates which oil is included in each formulation of phytosanitary composition exemplified.

TABLE 2

|  | Phytosanitary compositions | | | | |
|---|---|---|---|---|---|
|  | 1 (according to the invention) DEV1781 | 2 (comparative example) G400H | 3 (comparative example) Calumet/ Banole HV | 4 (comparative example) Spraytex | 5 (according to the invention) DEV1781 |
| Hydrocarbon-based oil A | X |  |  |  | X |
| Hydrocarbon-based oil B |  | X |  |  |  |
| Hydrocarbon-based oil C |  |  | X |  |  |
| Hydrocarbon-based oil E |  |  |  | X |  |

Evaluation of the Phytosanitary Compositions
Evaluation Method:

The evaluation was carried out on various plots of banana plants subject to Sigatoka disease.

Each plot is treated by mechanical sprinkling of the emulsified compositions. These oil-in-water emulsions are formulated by means of an emulsifier conventionally used in the field of the invention, called Imbirex® CR80SL, sold by the company Bayer CropScience. This type of emulsifier has no direct action that is active on the treatment of the plantations.

The treatments are repeated at a frequency and for a period which are detailed for each test phase and are applied randomly to the plots. Each plant was the subject of a detailed observation.

On the banana plants observed, the values of the following four parameters were determined each week:
 the total leaf number per tree,
 the youngest leaf with streaks. The streaks are lesions of elongated shape which are brownish-red in color,
 the youngest leaf with necrosis. The necroses are formed by the enlarging and the coalescence of the streaks,
 the disease severity index.

The leaves of the banana plants are classified as a function of their date of appearance on the plant and of the nodes on the trunks. The youngest leaf is leaf number 1. The leaves at the top of the trunk are the youngest and the lowest leaves are the oldest.

The response to the treatment is evaluated by means of the Stover scale modified according to Gauhl, described in table 3.

TABLE 3

| Disease stage | Description |
|---|---|
| 0 | No symptom |
| 1 | From several streaks to a maximum of 10 necroses |
| 2 | From 11 areas with necrosis to 5% of the surface of the infected leaf |
| 3 | 6-15% of the surface of the infected leaf |
| 4 | 16-33% of the surface of the infected leaf |
| 5 | 34-50% of the surface of the infected leaf |
| 6 | More than 50% of the surface of the infected leaf |

The appearance of the first symptoms correlates with the severity of the infection: the younger the infected leaf, the higher the level of severity of the infection.

Test Phase 1: Normal-Paraffin Contents/Biological Efficacy Relationship

This series of tests is carried out in order to demonstrate the efficacy of the composition according to the invention and the effect of the normal-paraffin content of the composition.

This series of tests is carried out on large plots of crops in order to specifically reproduce commercial practice. The compositions evaluated are combined with various types of fungicides. The fungicides are used in alternation in the compositions in order to avoid any phenomenon of resistance or of adaptation.

The tests are carried out on 4 plots of 780 m², at a rate of one plot per phytosanitary composition, each one comprising 105 plants. Each plot is surrounded by borders planted with banana plants of *Musa textilis* type, resistant to black Sigatoka disease, so as to avoid contaminations between plots.

In this series of tests, the 4 plots are treated according to a program corresponding to commercial practice. Thus, a comparison is made between two non-dewaxed oils in compositions 1 and 5 according to the invention and composition 2 and also two dewaxed oils in compositions 3 and 4. The non-dewaxed oil of compositions 1 and 5 according to the invention contains a high content of normal paraffins compared with composition 2.

Formulation and Plot Treatments

For each hectare of plantation, 23 liters of phytosanitary composition formulated as below are spread by sprinkling:
- 3, 5 or 7 liters of composition of phytosanitary oil A, B, C or D,
- this amount is reduced to 2.4, 4 or 5.6 liters of composition of phytosanitary oil A for composition 5,
- 16, 18 or 20 liters of water (to make the volume up to 23 liters in total),
- composition 5 comprises 17.4, 19 or 20.6 liters of water (to make the volume up to 23 liters in total),
- 0.05 liters of emulsifier.

The amount of composition of phytosanitary oil A, B, C or D is adjusted by those skilled in the art for each application, in particular as a function of the climatic conditions.

The amount of treatment is therefore 3, 5 or 7 liters of composition of phytosanitary oil per hectare as a mixture in water with 1% of emulsifier for an overall treatment volume of 23 liters of phytosanitary composition per hectare for compositions 1 to 4.

The amount of treatment is 2.4, 4 or 5.6 liters of composition of phytosanitary oil per hectare as a mixture in water with 1% of emulsifier for an overall treatment volume of 23 liters of phytosanitary composition per hectare for composition 5. The various fungicides were included in the phytosanitary compositions in an alternating manner in order to avoid the development of resistance. The lists of these fungicides, and also the frequency of use thereof, are the following:
- triazoles: 9 days
- amines and anilopyrimidines: 7 days
- protective compounds (mancozeb): 6 days.

TABLE 4 nature and amount of commercial fungicidal composition applied

| Trade name | Active ingredient | Chemical family | Amount of commercial product applied (l/ha) |
| --- | --- | --- | --- |
| Opus 12.5 SC | Epoxiconazole | DMI (demethylation inhibitors) | 0.8 |
| Sico 250 EC | Difenoconazole | DMI | 0.4 |
| Silvacur 30 EC | Tebuconazole + triadimenol | DMI + amines | 0.4 |
| Tilt 250 EC | Propiconazole | DMI | 0.4 |
| Volley 88 OL | Fenpropimorph | Amines | 0.5 |

TABLE 4-continued nature and amount of commercial fungicidal composition applied

| Trade name | Active ingredient | Chemical family | Amount of commercial product applied (l/ha) |
| --- | --- | --- | --- |
| Calixin 86 OL | Tridemorph | Amines | 0.5 |
| Impulse 80 EC | Spiroxamine | Amines | 0.4 |
| Siganex 60 SC | Pyrimethanil | AP (anilinopyrimidines) | 0.5 |
| Cumora 50 SC | Boscalid | (SDHI) succinate dehydrogenase inhibitors | 0.3 |
| Dithane 60 SC | Mancozeb | Dithiocarbamates | 2.0 |

The treatments are repeated by interval of fungistatic treatment according to the order indicated above. The amounts of fungicide administered are set out in table 4. The frequency of treatment is one application every 6 to 9 days. Each banana plant was the subject of detailed observation for each of the emulsions for a total period of 40 weeks. At the end of these 40 weeks, the condition of the plants was analyzed and then the plants were cut. A second treatment campaign was reiterated two weeks after cutting the first generation of plants, for a period of 38 weeks. The condition of the plants was evaluated after 15 weeks of the second treatment campaign.

Observation: the sequence of application of the fungicides is adjusted by those skilled in the art, based on the recommendations of the Fungicide Resistance Action Committee (FRAC: http://www.frac.info/working-group/banana-group/banana-frac-guidelines-2014-summary-table Results:

Table 5 indicates the mean of the results obtained in the first treatment campaign (first-generation plants) for each parameter evaluated.

TABLE 5

| Treatments | Age of the youngest leaf with streaks | Age of the youngest leaf with necrosis | Number of leaves in total | Severity |
| --- | --- | --- | --- | --- |
| Composition 1 DEV1781 | 7.4 | 9.8 | 13.5 | 0.16 |
| Composition 2 G400H | 6.6 | 8.4 | 13.5 | 0.42 |
| Composition 3 Calumet/banole HV | 6.9 | 8.6 | 13.5 | 0.34 |
| Composition 4 Spraytex | 6.5 | 8.2 | 13.4 | 0.49 |

The severity indices show that the results obtained on the banana plants treated with composition 1 according to the invention, which comprises a higher content of normal paraffins, are much better than those of the other compositions. Indeed, for the banana plants treated with composition 1 according to the invention, the disease is more than two times less severe than with composition 3 and more than 2.5 to 3 times less severe than with compositions 2 and 4. The treatment of the plots with composition 1 according to the invention therefore makes it possible to reduce the effects of the fungus and to guarantee the crop production.

Table 6 indicates the mean of the results obtained in the second treatment campaign (second-generation plants) for each parameter evaluated.

TABLE 6

| Treatments | Age of the youngest leaf with streaks | Age of the youngest leaf with necrosis | Number of leaves in total | Severity |
|---|---|---|---|---|
| Composition 1 | 7.8 | 9.3 | 12.1 | 0.34 |
| Composition 5 DEV1781 | 7.0 | 8.6 | 11.8 | 0.50 |
| Composition 3 Calumet/banole HV | 7.1 | 8.7 | 12.4 | 0.53 |
| Composition 4 Spraytex | 6.4 | 8.0 | 11.8 | 0.69 |

The severity indices show that the results obtained on the banana plants treated with composition 1 according to the invention, which comprises a high content of normal paraffins, are much better than those of the other compositions. Composition 5, which comprises a lower content of hydrocarbon-based oil according to the invention, shows results that are entirely acceptable in terms of control of the effects of the fungus.

The invention claimed is:

1. A phytosanitary composition comprising at least one paraffinic hydrocarbon fraction which comprises isoparaffins, normal paraffins and naphthenes, the weight content of naphthenes ranging from 10% to 50% relative to the total weight of the composition, the weight ratio of the normal paraffins relative to the weight of the isoparaffins being greater than or equal to 0.30, in a carrier suitable for the phytosanitary treatment of plants, the carrier consisting of an oil-in-water emulsion, a water-in-oil emulsion, a dispersion or a suspension of oily particles in an aqueous phase, wherein the hydrocarbon fraction has a pour point of greater than or equal to −5° C. according to the standard ASTM D97.

2. The phytosanitary composition as claimed in claim 1, wherein the hydrocarbon fraction comprises a weight content of normal paraffins of greater than or equal to 15%, relative to the total weight of the hydrocarbon fraction.

3. The phytosanitary composition as claimed in claim 1, wherein the hydrocarbon fraction comprises a weight content of isoparaffins of less than 75%, relative to the total weight of the hydrocarbon fraction.

4. The phytosanitary composition as claimed in claim 1, wherein the hydrocarbon fraction comprises a weight content of naphthene compounds ranging from 15% to 45%, relative to the total weight of the hydrocarbon fraction.

5. The phytosanitary composition as claimed in claim 1, wherein the hydrocarbon fraction is chosen from hydrocarbon-based chains comprising from 15 to 30 carbon atoms.

6. The phytosanitary composition as claimed in claim 1, wherein the hydrocarbon fraction comprises a weight content of unsulfonatable residues of greater than or equal to 92%, relative to the total weight of the hydrocarbon fraction.

7. The phytosanitary composition as claimed in claim 1, wherein the hydrocarbon fraction has a boiling point ranging from 250 to 400° C. according to the standard ASTM D86.

8. The phytosanitary composition as claimed in claim 1, wherein the hydrocarbon fraction has a kinematic viscosity at 40° C. ranging from 4 to 25 mm$^2$/s according to the standard ASTM D445.

9. The phytosanitary composition as claimed in claim 1, wherein the hydrocarbon fraction represents an amount ranging from 1% to 99% by weight relative to the total weight of the composition.

10. The phytosanitary composition as claimed in claim 1, which is in the form of an oil-in-water emulsion or of a water-in-oil emulsion.

11. An emulsifiable concentrated composition, that can be used for the preparation of a phytosanitary composition as claimed in claim 10, comprising:
at least one paraffinic hydrocarbon fraction which comprises isoparaffins, normal paraffins and naphthenes, the weight content of naphthenes ranging from 10% to 50% relative to the total weight of the composition, the weight ratio of normal paraffins relative to the weight of isoparaffins being greater than or equal to 0.30, wherein the hydrocarbon fraction has a pour point of greater than or equal to −5° C. according to the standard ASTM D97,
and
at least one emulsifier.

12. A method for the phytosanitary treatment of plants comprising applying to the plants the composition of claim 1.

13. The method of claim 12, wherein the composition is applied by sprinkling, spraying, or spreading on the crops.

14. The method as claimed in claim 12, for the preventive and/or curative treatment of cryptogamic diseases of plants.

15. The method as claimed in claim 14, for the preventive and/or curative treatment of cryptogamic diseases of plants of tropical and equatorial regions.

16. The method as claimed in claim 14, for the preventive and/or curative treatment of cryptogamic diseases of the banana plant.

17. The method as claimed in claim 16, for reducing, limiting, preventing, avoiding the development of black Sigatoka disease or black leaf streak disease of the banana plant, caused by the ascomycete fungus *Mycosphaerella fijiensis* and/or of yellow Sigatoka disease caused by the ascomycete fungus *Mycosphaerella musicola*.

18. The method of claim 12, further comprising the joint application of at least one fungicidal active ingredient.

\* \* \* \* \*